United States Patent [19]

Reynolds, Jr.

[11] 4,165,322

[45] Aug. 21, 1979

[54] ALKYLATION OF ANILINE WITH A LACTONE IN THE PRESENCE OF WATER

[75] Inventor: Richard N. Reynolds, Jr., Albany, Calif.

[73] Assignee: Chevron Research Company, San Francisco, Calif.

[21] Appl. No.: 847,503

[22] Filed: Nov. 1, 1977

[51] Int. Cl.² .................... C07D 307/32; C07D 333/36
[52] U.S. Cl. ..................................... 260/343.6; 549/63; 549/62
[58] Field of Search ..................... 260/343.6, 332.3 R, 260/332.3 AL

[56] References Cited

U.S. PATENT DOCUMENTS

| | | | |
|---|---|---|---|
| 2,650,231 | 8/1953 | Arnold | 260/343.6 |
| 3,002,976 | 10/1961 | Janssen | 260/332.3 R |
| 3,097,206 | 7/1963 | Zirkle | 260/332.3 R |
| 3,484,457 | 12/1969 | Mushowski | 260/343.6 |
| 3,639,385 | 2/1972 | Weaver | 260/332.3 R |
| 3,933,860 | 1/1976 | Chan | 260/343.6 |

FOREIGN PATENT DOCUMENTS 659483  11/1949  United Kingdom .................. 260/343.6

*Primary Examiner*—Natalie Trousof
*Assistant Examiner*—Jane T. Fan
*Attorney, Agent, or Firm*—D. A. Newell; T. G. DeJonghe

[57] ABSTRACT

A process for producing a lactone-substituted aniline wherein an alpha-halo-gamma-butyrolactone is reacted with an aniline in the presence of water at a temperature between 80° and 160° C. Thus, 3-(N-2,6-dimethylphenylamino)-gamma-butyrolactone is prepared by reacting an alpha-halo-gamma-butyrolactone with 2,6-dimethylaniline in the presence of water and an inert organic solvent at a temperature between 80° and 160° C. This process is advantageously combined with a subsequent acylation step to provide a continuous means for making materials such as 3-(N-chloroacetyl-N-2,6-dimethylphenylamino)-gamma-butyrolactone.

9 Claims, No Drawings

ALKYLATION OF ANILINE WITH A LACTONE IN THE PRESENCE OF WATER

BACKGROUND OF THE INVENTION

According to the present invention, a process is provided for reacting an aniline compound with a lactone. This reaction is referred to herein as an "alkylation" reaction. The term "alkylation" is thus used herein to refer to an addition reaction between an aniline and a lactone.

The compounds prepared in accordance with the process of the present invention are especially useful as fungicides.

Commonly assigned U.S. Pat. No. 3,933,860 discloses the preparation of lactone-substituted compounds wherein in a first step the following reaction is carried out

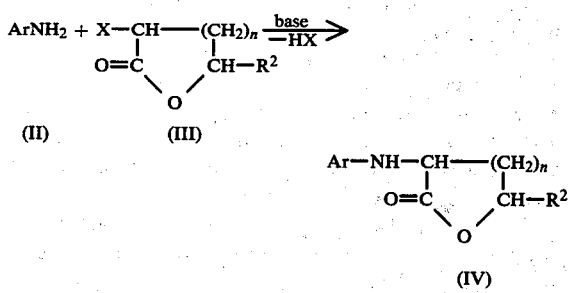

As can be seen from the examples in U.S. Pat. No. 3,933,860, the aniline reaction is carried out in the absence of water. Thus, in Example 1, dichloroaniline is reacted with alpha-bromo-gamma-butyrolactone at 110° to 145° C. to give a solid mixture of 3,4-dichloroaniline hydrobromide salt and 3-(N-3,4-dichlorophenylamino)-gamma-butyrolactone. The mixture thus obtained was treated with methylene chloride and filtered to separate the salt as a solid. The filtrate was evaporated to thereby remove the methylene chloride and yield the desired aniline-lactone reaction product.

In Example 2 of U.S. Pat. No. 3,933,860, dimethylaniline was reacted with alpha-bromo-gamma-butyrolactone in the presence of sodium carbonate and dimethylformamide. The reaction time was 21 hours. After the reaction, the reaction mixture was diluted with water at room temperature to remove the dimethylaniline hydrobromide salt into the aqueous phase and the reaction mixture was also extracted with benzene to remove the desired anilinelactone product into the organic, that is, benzene phase, then the benzene phase was separated and processed to separate the aniline-lactone product from the benzene phase.

H. Pleininger, Chemische Berichte, V. 83, p. 265-268 (1950), discusses cleavage of gamma-lactones with alkyl mercaptides. Pleininger discloses in his experimental section the conversion of dibromobutyric acid, in the absence of aniline and at low pH, to alpha-bromo-butyrolactone by heating with water at reflux temperature. Pleininger shows that the reaction between alpha-bromo-gamma-butyrolactone and aqueous ammonia gives initially gamma-hydroxy-alpha-amino butyric acid amide, which is then saponified and cyclized to alpha-amino-gamma-butyrolactone in two addition steps. In Plieninger's work, carbonyl attack (amido formation) competes with displacement of bromide (alkylation).

Frankel et al [Israel J. Chem. 1, 379–84 (1963)] found that carbonyl attack on, and resulting ring opening of, alpha-bromo-gamma-butyrolactone by aniline is favored over bromide displacement (alkylation) at high temperature (100° C. vs. 0° ). In Frankel, an excess of aniline was contacted with alpha-bromo-gamma-butyrolactone to give alpha-phenylamino-gamma-butyrolactone after aniline hydrobromide salt was removed. The alpha-phenylamino-gamma-butyrolactone was stirred with a 10% aqueous solution of sodium hydroxide resulting in hydrolysis or fission of the lactone ring to yield alpha-phenylamino-gamma-hydroxy butyranilide.

SUMMARY OF THE INVENTION

According to the present invention, a process is provided for making a compound of the formula

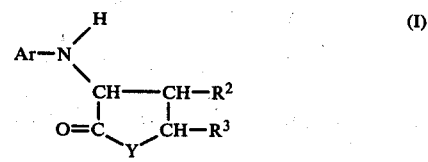

wherein
Ar is phenyl or phenyl substituted with the same or different subsituents selected from 1 to 5 alkyl or alkoxy groups of 1 to 4 carbon atoms; 1 to 2 fluoro, chloro or bromo; and 1 nitro;
$R^2$ and $R^3$ individually are hydrogen or alkyl of 1 to 4 carbon atoms; and Y is O or S which comprises: reacting a lactone or thiolactone compound of the formula

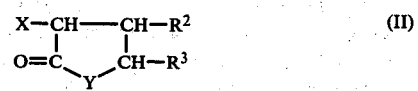

wherein X is chloro, iodo or bromo; Y is O or S; and $R^2$ and $R^3$ are as previously defined;
with an aniline compound, unsubstituted or substituted in the aromatic ring with the same or different substituents selected from 1 to 5 alkyl or alkoxy groups of 1 to 4 carbon atoms; 1 to 2 fluoro, chloro or bromo; and 1 nitro, in the presence of water and an inert organic solvent at a temperature between 80° and 160° to form the compound of Formula I.

Among other factors, the present invention is based on my finding that unexpectedly high yields of the alkylated aniline are obtained when the reaction is carried out in water at a temperature greater than 80° C. The reasons why the prior art did not carry out the alkylation reaction in the presence of water include the concern that water, in the presence of an organic base such as aniline, might cause scission of the lactone, e.g., to form an open-chain acid or amide. The gamma-hydroxy butyric acid formed by hydrolysis could then form a water-soluble salt with the aniline. The salt would be removed from the organic phase and into the aqueous phase. In the aqueous phase, aniline has low solubility and alkylation of the gamma-hydroxy butyric acid salt would be less likely to proceed.

Also, the water may cause premature splitting off of the halogen group from the lactone. Both of the foregoing reasons could be expected to be contributive of low yields when alkylating the aniline with the alpha-bromo-lactone.

The rate of alkylation in the presence of water was found to be comparable to the rate of alkylation in the absence of water when the reaction temperature and concentration of reactants in the organic phase was identical for each method.

I have found that the alkylation reaction in the presence of water in accordance with the present invention is especially advantageous in that the process is readily adaptable to continuous production of the lactone-aniline product. Alkylation in the absence of water must be done by a batch process. Salts formed during the alkylation in the absence of water must be first dissolved in water before transferring the product and salts out of the reaction vessel.

According to a preferred embodiment of the present invention, the lactone reactant is one wherein X is chloro or bromo, especially bromo, Y is O or S and $R^2$ and $R^3$ are hydrogen or methyl; and the aniline reactant is a 2,6-substituted aniline compound wherein the substituents at the 2- and 6-positions are methyl, ethyl or propyl. The terminology "hydrogen or methyl" means $R^2$ and $R^3$ may be the same or different. Preferably $R^2$ and $R^3$ are hydrogen.

The solvent used in the process of the present invention should be an organic solvent which is inert to reaction with aniline under the process conditions. Thus, 2,4-dichloroethane has been found not to be suitable. Also, the solvent should be substantially immiscible in water.

Particularly preferred solvents for the alkylation reaction of the present invention include aromatic hydrocarbons such as benzene, toluene, xylene and haloaromatics such as chlorobenzene and chloronaphthalenes. Toluene is an especially preferred solvent.

The alkylation reaction may be carried out at 50° to 200° C. However, I have found that 80° to 160° C. is preferable. Particularly preferred temperatures for the process of the present invention are 90° to 140° C.

Preferred pressures are atmospheric to 100 psig.

Preferred ratios for the feed constituents to the process of the present invention are 1 mol of the lactone, 1 to 6 mols of the aniline, 1 to 40 mols of water and 1 to 30 mols of the inert organic solvent. More preferred ratios for the feed constituents to the alkylation reaction of the present invention are 1 mol of the lactone, 2 to 2.2 mols of the aniline, 10 to 13 mols of the water and 1.7 to 2.3 mols of the inert organic solvent.

According to a particularly preferred embodiment of the present invention, a process is provided for making 3-(N-2,6-dimethylphenylamino)-gamma-butyrolactone which comprises reacting alpha-halo-gamma butyrolactone, wherein the halo group is bromo or chloro, with 2,6-dimethylaniline in the presence of water and an inert organic solvent at a temperature between 80° and 160° C. to form 3-(N-2,6-dimethylphenylamino)-gamma-butyrolactone in an organic phase of a two-phase aqueous-organic mixture.

Preferably the halo group of the lactone reactant is bromo. Preferably the organic solvent is toluene, and preferably the reaction temperature is between 90° and 140° C.

Preferred ratios for the above-mentioned feed constituents to the reaction zone are 1 mol of the lactone, 2 to 2.2 mols of the aniline, 10 to 13 mols water, 1.7 to 2.3 mols toluene. Broader suitable ranges are 1 mole of the lactone, 1 to 6 moles of the aniline, 1 to 40 mols water, and 1 to 30 mols inert organic solvent, such as toluene.

I have found that especially high yields are achieved in the process of the present invention if the molar ratio of lactone to aniline is approximately one to one and the pH is maintained at about 7.0, for example between about 6 and 8, by adding a base such as sodium carbonate at a sufficient rate to so maintain the pH during the alkylation reaction.

EXAMPLES

Example 1

Preparation of 3-(N-2,6-dimethylphenylamino)-gamma-butyrolactone

An aqueous/toluene mixture of alpha-bromo-gamma-butyrolactone and dimethylaniline in a molar ratio of one mol lactone to 2.1 mols of aniline was heated with stirring at 92° C. for 18 hours. This resulted in the reaction of the lactone with the aniline compound to obtain 3-(N-2,6-dimethylphenylamino)-gamma-butyrolactone in the organic phase. The aqueous phase contained excess dimethylaniline combined with hydrogen bromide to thus form a salt. The aqueous phase containing the dimethylaniline hydrogen bromide salt was phase-separated from the organic phase.

The organic phase was washed with an aqueous solution containing 5% hydrochloric acid to remove residual dimethylaniline. Water was azeotropically distilled from the organic phase, i.e., toluene solution containing 3-(N-2,6-dimethylphenylamino)-gamma-butyrolactone.

The composition of the toluene mixture before and after the reaction of the bromobutyrolactone with dimethylaniline is summarized in Table I below:

TABLE I

| Component | Before (wt.%) | After Reaction of Product (wt.%) |
| --- | --- | --- |
| Bromobutyrolactone | 19.2 | 1.5 |
| Dimethylaniline | 29.7 | — |
| Toluene | 22.3 | 51.2 |
| Bromobutyrolactone impurities | 3.2 | — |
| 3-(N-z,6-dimethylphenylamino)-gamma-butyrolactone | | 40.8 |
| 3-(N-2,6-dimethylphenylamino)-gamma-butyrolactone impurities | | 6.5 |

Example 2

This example illustrates the alkylation reaction with and without water.

A. A mixture of 180.3 g (1.0 mol) of alpha-bromo-gamma-butyrolactone (91.5% a.i.), 254.1 g (2.1 mol) of 2,6-dimethylaniline, 200 ml toluene and 200 ml water was heated to 90° C. for a total of 23.25 hours. Samples of the toluene layer were removed periodically and analyzed for bromobutryolactone (BBL), dimethylaniline (DMA), and alkylation product.

B. A second mixture of reagents, identical with the first except for the omission of water, gave similar results (within experimental error). Reaction aliquots were water washed before analysis.

The results of both runs are summarized below in Table II.

TABLE II

| | BBL:DMA:Alkylation Product (wt.% in Toluene) | |
|---|---|---|
| Time (hrs.) at 90° C. | With Water Run A | Without Water Run B |
| 0 | 22.7:37.2:6.4 | 20.3:37.7:9.3 |
| 0.5 | 19.6:33.3:11.1 | 19.0:31.8:15.3 |
| 1.0 | 17.5:31.1:15.6 | 15.1:27.4:18.4 |
| 1.5 | 17.1:29.3:18.8 | 16.6:26.7:21.2 |
| 2.0 | 14.7:27.3:20.5 | 14.3:23.8:26.1 |
| 2.5 | 13.4:24:0:23.1 | 11.9:19.0:27.4 |
| 3.0 | 11.7:22.5:27.3 | 10.8:17.7:29.8 |
| 3.4 | 10.7:20.7:27.5 | 9.8:15.5:32.8 |
| 4.0 | 9.0:18.4:31.7 | 9.3:14.9:33.9 |
| 5.0 | 8.5:17.4:32.9 | 8.1:13.4:36.8 |
| 6.0 | 6.5:14.5:37.2 | 7.6:12.2:38.3 |
| 7.0 | 6.0:12.2:37.0 | 6.8:11.4:39.8 |
| 23.25 | 1.3: 5.2:48.4 | 1.3: 3.9:51.7 |
| Product Purity | 1.2: 0.7:92.6 | 1.7: 0.7:93 |

The product purity indicated in Table I was obtained after acid washing of the organic (toluene) phase in 200 ml of HCl followed by washing in 60 ml of hot water and finally by stripping (vacuum drying).

The reaction mixture (B) without water initially present was much darker than Run A (with water) before and after water wash.

What is claimed is:

1. A process for making a compound of the formula

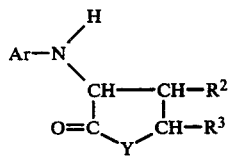
(I)

wherein
Ar is phenyl or phenyl substituted with the same or different subsituents selected from 1 to 5 alkyl or alkoxy groups of 1 to 4 carbon atoms; 1 to 2 fluoro, chloro or bromo; and 1 nitro;
$R^2$ and $R^3$ are hydrogen or alkyl of 1 to 4 carbon atoms; and Y is 0 or S which comprises:
reacting a lactone or thiolactone compound of the formula

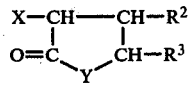
(II)

wherein X is chloro, iodo or bromo; Y is O or S; and $R^2$ and $R^3$ are as previously defined;
with an aniline compound, unsubstituted or substituted in the aromatic ring with the same or different substituents selected from 1 to 5 alkyl or alkoxy groups of 1 to 4 carbon atoms; 1 to 2 fluoro, chloro or bromo; and 1 nitro, in the presence of water and an inert organic solvent at a temperature between 80° and 160° to form the compound of Formula I in a reaction zone and wherein the lactone or thiolactone compound and the water are fed to the reaction zone in a ratio of 1 mol of the lactone or thiolactone per 1–40 mols of the water.

2. A process in accordance with claim 1 wherein: X is chloro or bromo; Y is O or S; $R^2$ and $R^3$ are hydrogen or methyl; and the aniline compound is a 2,6-substituted aniline compound wherein the substituents at the 2- and 6-position are methyl, ethyl or propyl.

3. A process in accordance with claim 2 wherein X is bromo.

4. A process in accordance with claim 2 wherein the solvent is toluene and X is bromo.

5. A process in accordance with claim 1 for making 3-(N-2,6-dimethylphenylamino)-gamma-butyrolactone which comprises reacting alpha-halo-gamma-butyrolactone, wherein the halo group is bromo or chloro, with 2,6-dimethylaniline in the presence of water an an inert organic solvent at a temperature between 80° and 160° C. to form 3-(N-2,6-dimethylphenylamino)-gamma-butyrolactone in an organic phase of a two-phase aqueous-organic mixture.

6. A process in accordance with claim 5 wherein the halo group is bromo.

7. A process in accordance with claim 6 wherein the solvent is toluene.

8. A process in accordance with claim 7 wherein the temperature is between 90° and 140° C.

9. A process in accordance with claim 7 wherein the reaction of the butyrolactone with dimethylaniline is carried out in a reaction zone and with the ratio of feed constitutents to the reaction zone comprising: one mol of the butyrolactone, 2 to 2.2 mols dimethylaniline, 10 to 13 mols water and 1.7 to 2.3 mols toluene.

* * * * *